United States Patent
Brown et al.

(10) Patent No.: US 11,324,483 B2
(45) Date of Patent: May 10, 2022

(54) VOLUMETRIC ULTRASOUND IMAGE DATA REFORMATTED AS AN IMAGE PLANE SEQUENCE

(71) Applicant: KONINKLIJKE PHILIPS N.V., Eindhoven (NL)

(72) Inventors: Jimmy Ray Brown, Snohomish, WA (US); Kevin Bradley, Bothell, WA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 157 days.

(21) Appl. No.: 16/261,746

(22) Filed: Jan. 30, 2019

(65) Prior Publication Data
US 2019/0156936 A1 May 23, 2019

Related U.S. Application Data

(63) Continuation of application No. 13/636,613, filed as application No. PCT/IB2011/051125 on Mar. 17, 2011, now Pat. No. 10,235,497.
(Continued)

(51) Int. Cl.
*A61B 8/00* (2006.01)
*A61B 8/08* (2006.01)
(Continued)

(52) U.S. Cl.
CPC .............. *A61B 8/465* (2013.01); *A61B 8/466* (2013.01); *A61B 8/469* (2013.01); *A61B 8/483* (2013.01);
(Continued)

(58) Field of Classification Search
CPC ........ G16H 30/20; A61B 8/465; A61B 8/469; A61B 8/483; A61B 8/523; G01S 15/8993
See application file for complete search history.

(56) References Cited

U.S. PATENT DOCUMENTS 5,474,073 A 12/1995 Schwartz et al.
5,993,390 A 11/1999 Savord et al.
(Continued)

FOREIGN PATENT DOCUMENTS

CA 2583600 A1 4/2006
EP 0803227 A1 10/1997
(Continued)

OTHER PUBLICATIONS

"Digital Imaging and Communication in Medicine" (DICOM), Supplement 43: Storage of 3D Ultrasound Images, Annex X, Apr. 10, 2009 (Apr. 10, 2009), pp. 81-86, XP55001594, Rosslyn, VA, 22209, USA [retrieved on Jun. 29, 2011] cited in the application.
(Continued)

*Primary Examiner* — Jason M Ip

(57) ABSTRACT

An ultrasound probe acquires a 3D image dataset of a volumetric region of the body. The 3D image data is reformatted into a sequence of successive parallel image planes extending in one of three orthogonal directions through the volume. The sequence of images is preferably formatted in accordance with the DICOM standard so that a clinician can review the 3D image data as a sequence of DICOM images on an image workstation.

21 Claims, 4 Drawing Sheets

Related U.S. Application Data

(60) Provisional application No. 61/316,471, filed on Mar. 23, 2010.

(51) Int. Cl.
    *G01S 15/89*     (2006.01)
    *G16H 30/40*     (2018.01)
    *G16H 30/20*     (2018.01)
    *G01S 7/52*     (2006.01)

(52) U.S. Cl.
    CPC .......... *A61B 8/523* (2013.01); *G01S 15/8993* (2013.01); *G16H 30/20* (2018.01); *G16H 30/40* (2018.01); *G01S 7/52073* (2013.01); *G01S 7/52074* (2013.01)

(56) References Cited

U.S. PATENT DOCUMENTS

| | | |
|---|---|---|
| 6,117,080 A | 9/2000 | Schwartz |
| 6,511,426 B1 | 1/2003 | Hossack et al. |
| 6,572,547 B2 | 6/2003 | Miller et al. |
| 2004/0087853 A1 | 5/2004 | Fujisawa |
| 2005/0033160 A1 | 2/2005 | Yamagata et al. |
| 2005/0122343 A1 | 6/2005 | Bailey et al. |
| 2007/0129631 A1* | 6/2007 | Ma .................. A61B 8/463 600/437 |
| 2007/0269117 A1 | 11/2007 | Ernvik et al. |
| 2009/0267940 A1 | 10/2009 | Garg et al. |
| 2011/0157154 A1* | 6/2011 | Bernard .................. A61B 8/00 345/419 |

FOREIGN PATENT DOCUMENTS

| | | |
|---|---|---|
| WO | 03045222 A2 | 6/2003 |
| WO | 2006042163 A2 | 4/2006 |

OTHER PUBLICATIONS

Poulsen et al: "An Optical Registration Method for 3D Ultrasound Freehand Scanning", Ultrasonics Symposium, 2005 IEEE Rotterdam, The Netherlands Sep. 18-21, 2005, Piscataway, NJ, USA, IEEE, vol. 2, Sep. 18, 2005 (Sep. 18, 2005), pp. 1236-1240, XP010899187, DOI: DOI:10.1109/ULTSYM.2005.1603075 ISBN: 978-0-7803-9382-0 abstract; figures.

\* cited by examiner

VOLUMETRIC ULTRASOUND IMAGE DATA REFORMATTED AS AN IMAGE PLANE SEQUENCE

CROSS-REFERENCE TO RELATED APPLICATIONS

This application is a continuation of U.S. patent application Ser. No. 13/636,613, filed on Sep. 21, 2012, which is the U.S. National Phase Application under 35 U.S.C. § 371 of International Application No. PCT/IB2011/051125, filed on Mar. 17, 2011, which claims the benefit of Provisional Application Ser. No. 61/316,471, filed on Mar. 23, 2010. These applications are hereby incorporated by reference herein.

This invention relates to medical diagnostic ultrasound systems and, in particular, to ultrasound systems for three dimensional (3D) imaging which are capable of exporting volumetric image data as a sequence of planar images. Ultrasonic diagnostic imaging has traditionally scanned two-dimensional cross-sectional images of anatomy of the body. As the technology has developed, ultrasound can now scan and image three dimensional volumes, in both still images and real time. The 3D datasets of a scanned volume can be successively rendered as three dimensional views, rapidly enough for the clinician to observe the motion of the anatomy in real time movement. But radiologists and cardiologists are still more familiar with seeing the standard 2D planar images of anatomy and many are still not comfortable with diagnosing anatomy in 3D, a challenge made more difficult by the tissue clutter which often surrounds and obscures the region of interest at the center of the volume being imaged. As a result, many physicians prefer to see planar 2D image "slices" of a 3D volume. Once a 3D volume image dataset has been captured, a technique called multiplanar reformatting enables the clinician to select one or more cut planes through the volume for viewing as 2D images. In the typical user interface the clinician can position three orthogonal lines in the volume image. Each line represents the position of one of three orthogonal image planes through the volume, an x-y plane (azimuth vs. depth), a y-z plane (depth vs. elevation, generally referred to as a C plane), and an x-z plane (azimuth vs. elevation). As the lines are repositioned, 2D images of the corresponding cut planes are formed by the voxels of the dataset intercepted by the cut planes. See U.S. Pat. No. 6,572,547 (Miller et al.), which illustrates the use of such cut planes to visualize the tip of a catheter from the three different imaging perspectives.

A further limitation of three dimensional imaging is that the datasets of 3D images are formatted differently by various ultrasound imaging system vendors, as the vendors try to process and accommodate the storage of the large (3D) datasets inherent in three dimensional imaging. In an effort to align these different proprietary approaches, a working group of the DICOM Standards Committee published Supplement 43 to the standard in April, 2009 directed specifically to a DICOM standard for storing 3D ultrasound images. However implementation of this standard for 3D ultrasound images has not been rapid, and the plans of different vendors for converting imaging systems such as PACS systems to the new 3D standard remain largely unknown. Accordingly there remains a need to provide 3D image data in a standardized format which readily lends itself to transport and use on other medical image platforms which have not implemented the DICOM standard for 3D ultrasound images.

In accordance with the principles of the present invention, an ultrasound system is described which reformats 3D image data as one or more sequences of 2D images in respective cut plane directions which can be ported to other imaging platforms and replayed and diagnosed as a standardized 2D real time image sequence. A user interface provides selection of the cut plane direction, the spacing of the planes, and/or the number of images in the sequence. The volume is then reformatted into planar images in the selected cut plane direction(s) and stored as one or more image sequences, enabling replay of each sequence on most conventional medical imaging platforms, preferably as 2D DICOM image sequences.

Figure 1:
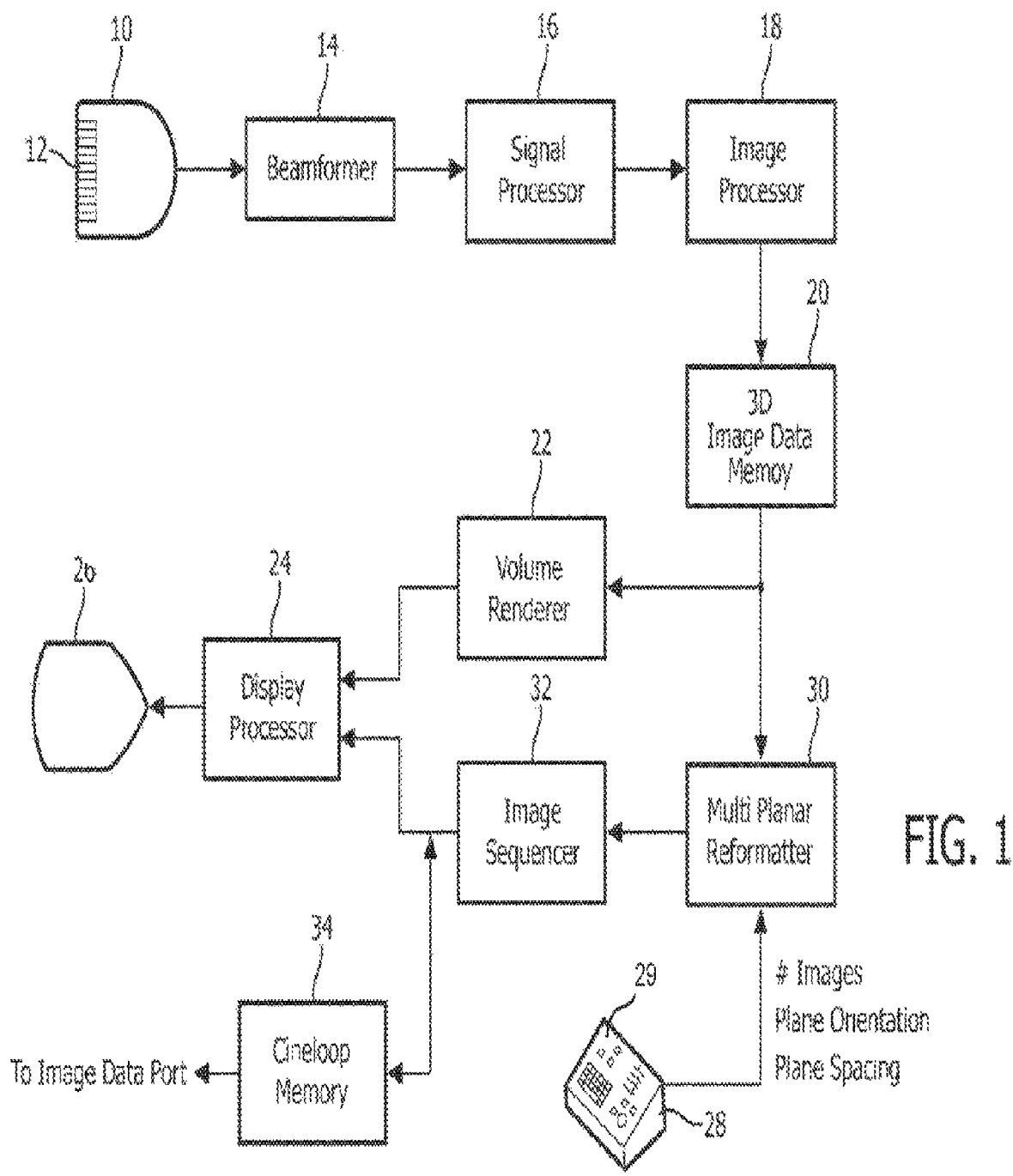
FIG. 1 illustrates in block diagram form an ultrasound system constructed in accordance with the principles of the present invention.

Referring to FIG. 1, an ultrasound system constructed in accordance with the principles of the present invention is shown in block diagram form. An ultrasound probe 10 with an array transducer 12 transmits ultrasound waves into the body of a patient and receives echoes from a volumetric region in response. Several techniques are known for ultrasonically scanning a volumetric region of the body. One is to move an ultrasound probe containing a one-dimensional array transducer over the skin in a direction normal to the image plane of the probe. The probe will thus acquire a succession of substantially parallel image planes as the probe is moved, and the image data of the image planes comprises a 3D image dataset. This manual technique, referred to as freehand scanning, is described in U.S. Pat. No. 5,474,073 (Schwartz et al.) A second technique is to mechanically oscillate the transducer array back and forth inside a compartment of the probe. The probe will thus acquire the same data from a succession of substantially parallel image planes as in the freehand technique, but in this case the mechanical oscillation of the transducer array may be rapid enough to produce real time 3D images. The third approach is to use a probe with a two-dimensional array transducer, from which beams can be electronically scanned in three dimensions by phased array beam steering. A 3D probe with a two-dimensional array for this purpose is described in U.S. Pat. No. 5,993,390 (Savord et al.) This third approach advantageously uses a probe with no moving parts, and electronic beam steering can be done rapidly enough to scan even the heart with real time imaging. Each of these scanning techniques is capable of producing a 3D image dataset suitable for use with the present invention.

The echo signals received by the individual transducer elements of the array 12 are processed by a beamformer 14 to form coherent echo signals relating to specific points in the body. The echo signals are processed by a signal processor 16. Signal processing may include separation of harmonic echo signal components for harmonic imaging and clutter removal, for example. The processed signals are arranged into images of a desired format such as a trapezoidal sector or a cube by an image processor 18. The 3D image data is organized by its x-y-z coordinates in the volumetric region and stored in an image memory 20. The 3D image data is rendered into a three-dimensional image by a volume renderer 22. A series of volume rendered images may be dynamically displayed in kinetic parallax so that the user may rotate, re-orient and reposition the volume from different viewing perspectives as described in U.S. Pat. No. 6,117,080 (Schwartz). The images are processed for display by a display processor 24 which can overlay the 3D image with graphics, and the image is displayed on an image display 26.

A 3D volumetric image can also be examined by "slicing through" the volume and displaying a particular slice as a 2D image. The location of the slice in the volume is selected by user manipulation of a control on a user control interface 28. The user control will select a particular 2D plane in the 3D volume as described above, and a multi-planar reformatter 30 selects the planar data of the 3D dataset which have coordinates in the selected plane. The 2D image of the selected plane is shown on the display 26, either alone or in conjunction with the 3D image. As previously described, the user control interface can present the user with three differently colored lines or cursors, each of which can select a plane of a respective mutually orthogonal orientation. The user can thus simultaneously view three orthogonal planes through the 3D volume, as described in U.S. Pat. No. 6,572,547 (Miller et al.), for example. In accordance with the principles of the present invention, the image data of a 3D volume is arranged in a sequence of images of sequential, parallel planes of the volume. The sequence of images may be stored as a sequence of frames within an ultrasound DICOM multi-frame image, which can be stored and replayed on most medical image workstations and PACS systems in the manner of a 2D image sequence stored in an ultrasound DICOM multi-frame image. A clinician can thereby view the image data of the 3D volume as a sequence of cut planes through the volume. The clinician can replay the image sequence rapidly, giving the impression of "swimming through" the volume. Or, the clinician can step through the sequence slowly or pick out a particular image in a plane which cuts through a region of interest for diagnosis. The 3D volume data can thus be reviewed as 2D images with which the clinician is more comfortable and familiar than a 3D volume image.

In the implementation of FIG. 1, the user operates the user control interface to select the orientation of the planes of the 2D image sequence (or sequences) to be created. Standard 2D images have an azimuth (x) dimension and a depth (y) dimension and the clinician may, for example, want to have the cut planes oriented in a succession of x-y planes, each with a different z (elevation) coordinate in the volume. This selection is applied to the multi-planar reformatter 30, which selects a sequence of x-y image planes of the 3D dataset. This sequence of x-y cut plane images is coupled to an image sequencer 32, which processes the images as a succession of 2D images. The image sequence can have a proprietary (custom) format used by the particular ultrasound system, but preferably the 2D images are processed in compliance with the DICOM standard for two-dimensional medical images. With DICOM standard formatting, the image sequence can be replayed and viewed on a wide variety of medical image platforms. The 2D image sequence is stored in a Cineloop® memory 34 as a sequence or "loop" of 2D images. The image sequence can be sent to other imaging systems and platforms by way of the image data port of the ultrasound system. An image sequence of the present invention can be ported to an image review workstation in another department of a hospital over the hospital's image data network, for instance.

In a preferred implementation of the present invention the user can specify and select additional parameters of the 2D image sequence of the 3D volume. As shown in FIG. 1, the user control interface 28 uses the same or other user controls to specify other characteristics of a 2D image sequence, including selecting the number of images of the sequence and the plane-to-plane spacing of the cut planes of the sequence. The user controls may also provide the ability for the user to select a particular sub-volume of the 3D volume for the cut planes. For example, the user may select just the central one-third of the volume for the 2D image sequence. As another example, the entire 3D volume is to be reformatted into 2D image planes in a sequence of 100 image planes. The multi-planar reformatter takes this selection and distributes the 100 cut planes at equal intervals over the volume in the selected orientation. As another example, the user selects a 2 mm plane-to-plane spacing, and the multi-planar reformatter cuts the 2D image planes at 2 mm intervals through the volume in the selected orientation.

Figure 2:
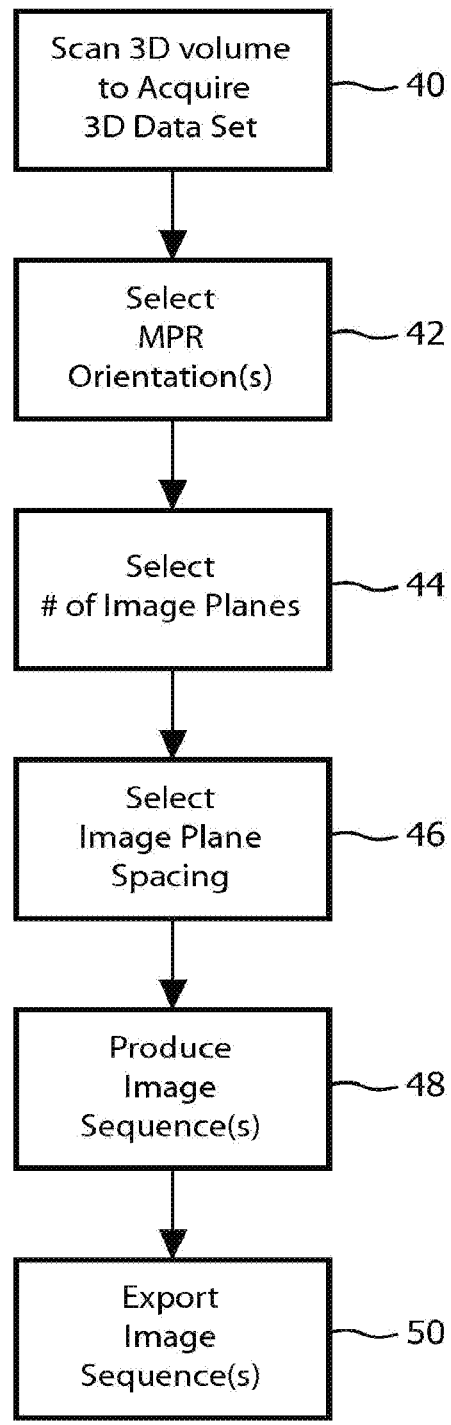
FIG. 2 illustrates a sequence for acquiring a 3D dataset and reformatting the data as one or more planar image sequences in accordance with the present invention.

FIG. 2 illustrates a process for producing and exporting a 2D image sequence of a 3D volume in accordance with the present invention. In step 40 the clinician scans a volumetric region of the body to acquire a 3D dataset. In step 42 the clinician observes the rendered 3D image and selects one or more plane orientations for one or more image sequences into which the volume is to be sliced by the multi-planar reformatter. The clinician may select two sequences, for example, one with the cut planes having x-y coordinates and another with the cut planes having y-z coordinates. In a constructed embodiment the selection of the plane orientation for a sequence is done by selecting and viewing a particular MPR image plane. The other images of the sequence will then be formatted in planes parallel to the selected plane. In step 44 the clinician selects the number of image planes of each sequence. The clinician may select 50 planes for the x-y plane sequence and 20 planes for the y-z plane sequence, for example. In step 46 the clinician selects the image plane spacing. The clinician may select a 1 mm spacing for the x-y planes and a 2 mm spacing for the y-z planes, for example. If the inter-plane spacing of this step is too large for the number of planes selected in step 44, the system will notify the user of the conflict so that the user can select one parameter or the other. If the inter-plane spacing selected is too small for the full volume, the system will distribute the number of plane selected with the selected inter-plane spacing about the center of the volume, where users most frequently position the region of interest. Alternatively, the user may specify a sub-region of the volume over which the planes are to be distributed. In the constructed embodiment there is no need to perform steps 44 and 46; the ultrasound system automatically produces planes of image data from one side of the 3D volume to the other, and produces image planes at the smallest plane-to-plane spacing permitted by the ultrasound system. In step 48 the multi-planar reformatter and the image sequencer produce the specified image sequence(s). In step 50 the image sequence(s) are exported to an image workstation as an ultrasound DICOM multi-frame image for review and diagnosis.

Figure 3:
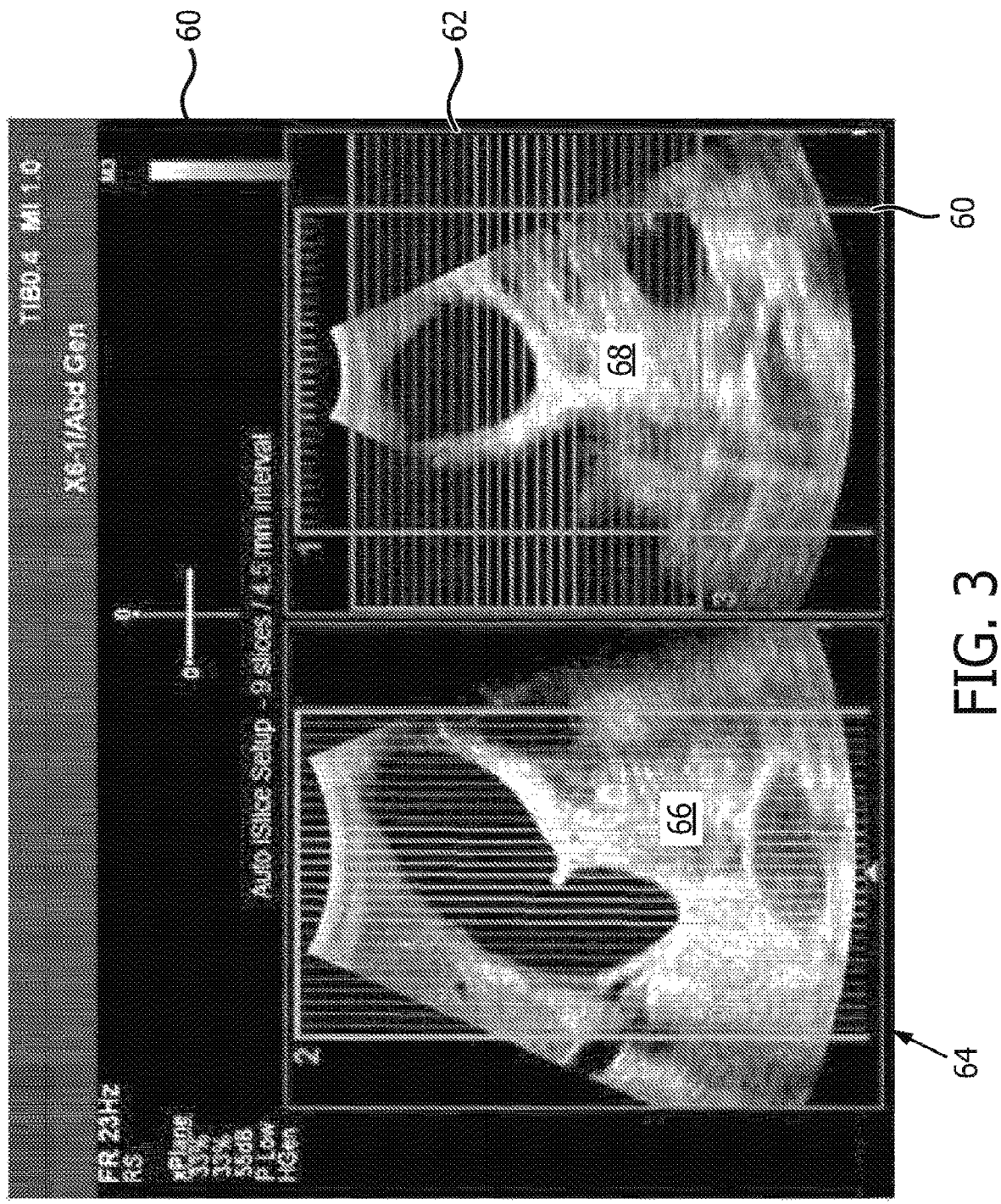
FIG. 3 illustrates lines over a 3D image indicating position of cut planes in accordance with the present invention.

FIG. 3 is an image display on the screen of display 26 which illustrates a grid of cut plane lines which show the user the planes which will be reformatted into sequences of 2D images. On the left side of the display screen 60 is an ultrasound image 66 which is oriented in the x-y plane. Overlaying this image 66 is a grid of vertical lines 64, which indicate a series of cuts through the volume in the y-z (elevation) direction. This grid 64 shows the user that the portion of the volume spanned by these thirty cut planes will be reformatted into a sequence of thirty 2D images in the y-z dimension. On the right side of the display is a second image 68 through the volume in the x-y dimension which is overlaid with a grid of horizontal lines 62. This grid 62 shows the user that a sub-region of the volume extending from near the top of the image down to about two-thirds of the full image depth will be reformatted into a sequence of thirty C-plane images, that is, images which are each in the x-z dimension and are at successive depths (y-direction increments) of the volume. The grid 62 is backed by a graphical box 60 which at the top indicates with small tick-marks the locations of the cut planes in the y-z dimension which is set over the left-side image 66. Thus, the user can see at a glance the relative locations of the two sets of orthogonal grid lines and cut planes.

The user is also given the ability to rotate or tilt a grid 62,64 and thereby create cut plane lines which are tilted or rotated with respect to the nominal orientation of purely horizontal or vertical cut planes.

Figure 4:
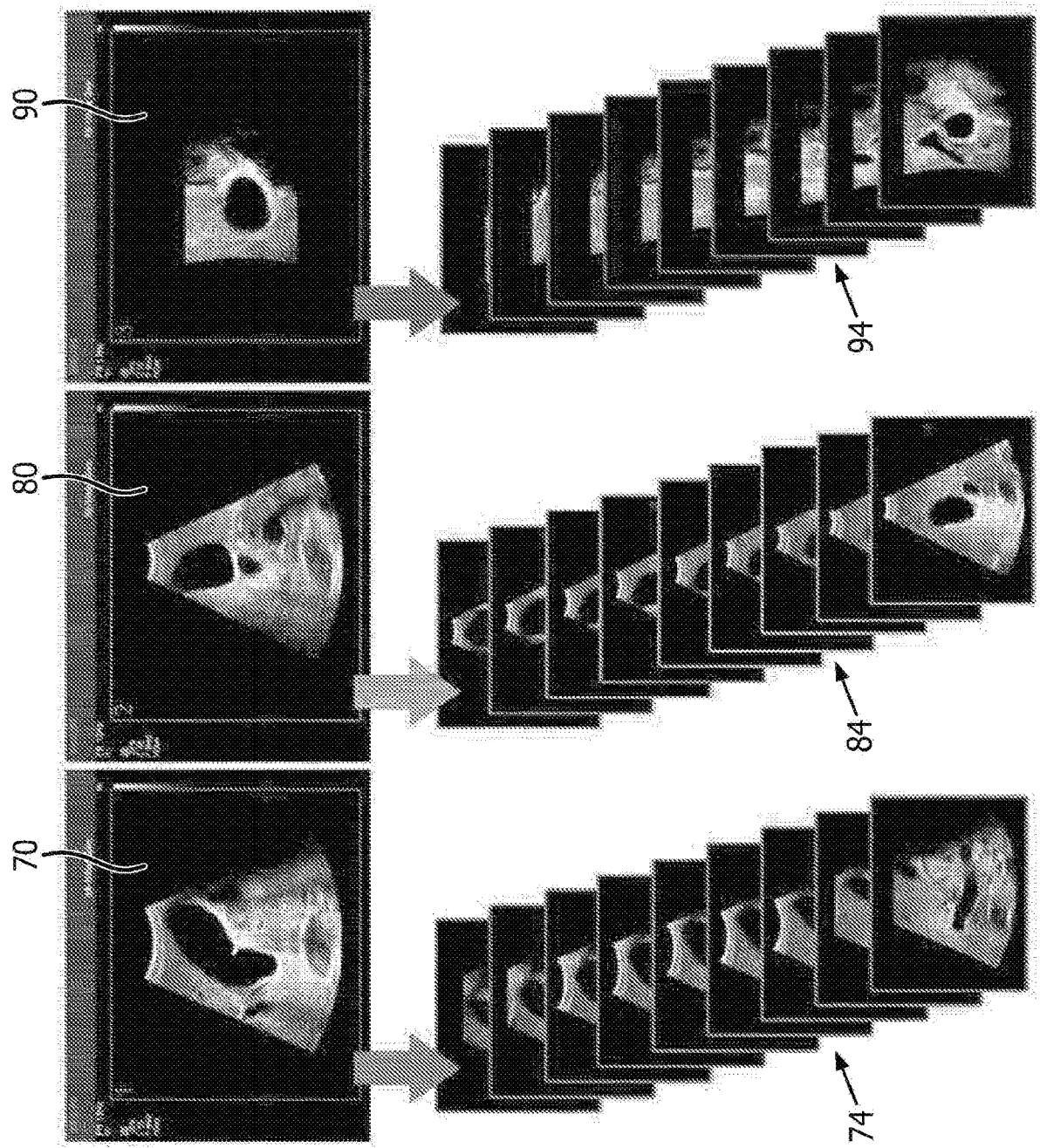
FIG. 4 illustrates the formation of three planar image sequences from a volumetric image dataset in accordance with the present invention.

FIG. 4 illustrates three image sequences 74, 84, 94 which are produced by an implementation of the present invention. The display screen 70 on the left side of FIG. 4 shows an ultrasound image 72 cut through the volume in the x-y dimension, and an image sequence 74 of 2D images which are in successive x-y planes through the volume and 3D dataset. In the center of FIG. 4 is a display screen 80 showing an image 84 in the y-z plane and below this image is an image sequence 84 of images in successive y-z cut planes through the volume and 3D dataset. On the right side of FIG. 4 is a display screen 90 showing a C-plane (x-z dimension) 92 and below it is a sequence 94 of images cut through successive x-z planes of the volume and 3D dataset. The three image sequences show images cut through mutually orthogonal planes of the volume and 3D dataset, one which progresses in the z direction, a second which progresses in the x direction, and the third which progresses in the y direction. The user can export one, two, or all three image sequences as DICOM images to an image workstation for further analysis and diagnosis.

Since each cut plane is through the full 3D image dataset, each 2D cut plane image thus intersects and contains all of the image data acquired for the particular reformatted image. In a preferred embodiment the 2D images are in Cartesian coordinates and each image sequence is of successive cut planes in a respective orthogonal Cartesian coordinate direction. The 2D images are thus suitable for measurement and quantification to the same degree as a standard 2D image acquired by conventional means by a one-dimensional array transducer.

What is claimed is:

1. An ultrasonic diagnostic imaging system configured to acquire a three dimensional (3D) image data of a volumetric region of a body and output a multi-frame image comprising a sequence of equally spaced two dimensional (2D) images in place of the 3D image data to represent the volumetric region in a memory, the system comprising:
    an ultrasound probe configured to acquire a 3D image dataset of the volumetric region;
    a display configured to display a volume rendering of the 3D image dataset;
    a user interface comprising a control and configured to receive an indication from a user, via the control, of a cutting direction through the 3D image dataset after the display displays the volume rendering;
    a multiplanar reformatter configured to automatically generate, responsive to the indication, a first plurality of 2D images at equally spaced planes through the 3D image dataset;
    an image sequencer configured to process the 2D images by arranging the first plurality of 2D images into a sequence of 2D images for storing the sequence of 2D images independent of the 3D image dataset; and
    a Cineloop memory which is configured to store the sequence of 2D images as a sequence of frames in a multi-frame image in which individual 2D images are stored, in sequential order, as individual frames of the multi-frame image for exporting from the ultrasonic diagnostic imaging system independent of the 3D image dataset.

2. The ultrasonic diagnostic imaging system of claim 1, wherein the first plurality of 2D images is automatically generated to include a sufficient number of 2D images such that an entire portion of the volumetric region is represented by the 2D images of the first plurality of 2D images.

3. The ultrasonic diagnostic imaging system of claim 2, wherein the sufficient number is based on a specified plane-to-plane spacing, a specified number of cut planes, or both.

4. The ultrasonic diagnostic imaging system of claim 1, further comprising a data port, coupled to the image sequencer, and configured to receive the multi-frame image comprising the sequence of 2D images for transferring the multi-frame image comprising the sequence of 2D images to another imaging system or to a storage device for subsequently visualizing or storing a representation of the volumetric region, without transferring or storing the 3D image dataset.

5. The ultrasonic diagnostic imaging system of claim 1, wherein the display is further configured to display one or more of the 2D image sequences.

6. The ultrasonic diagnostic imaging system of claim 1, wherein the multi-frame image is a DICOM multi-frame image.

7. The ultrasonic diagnostic imaging system of claim 1, wherein the multi-frame image is configured to enable a user to replay the sequence of 2D images on the display to give an impression of "swimming through" the volumetric region and is further configured to enable the user to step through individual ones of the 2D images for selecting a particular one of the 2D images.

8. The ultrasonic diagnostic imaging system of claim 1, wherein the indication of the cutting direction through the 3D dataset is generated responsive to user input.

9. The ultrasonic diagnostic imaging system of claim 8, wherein the indication of the cutting direction is generated responsive to a selection of a 2D image plane through the displayed volume rendering of the 3D image dataset.

10. The ultrasonic diagnostic imaging system of claim 8, wherein the user control interface is further configured to receive user input indicative of a specified plane-to-plane spacing.

11. The ultrasonic diagnostic imaging system of claim 10, wherein the user control interface is further configured to receive user input indicative of a specified number of cut planes, wherein the multiplanar reformatter is configured to automatically generate the first plurality of 2D images to include a number of equally spaced 2D images equal to the number of cut planes.

12. The ultrasonic diagnostic imaging system of claim 11, further comprising a display processor coupled to the display, wherein the display processor is configured to produce a graphic for overlaying the volume rendering, wherein the graphic is configured to provide an indication of spatial locations of the cut planes.

13. The ultrasonic diagnostic imaging system of claim 12, wherein the graphic comprises a grid of cut plane lines, and wherein the user interface is further configured to receive user input indicative of an adjustment of a number of the cut plane lines of the grid, a spacing of the cut plane lines of the grid, a position of the cut plane lines relative to the volume rendering, or a combination thereof.

14. The ultrasonic diagnostic imaging system of claim 13, wherein the user interface further comprises a user control by which a user can rotate or tilt the grid of cut plane lines relative to the volume rendering.

15. The ultrasonic diagnostic imaging system of claim 1, wherein the multiplanar reformatter is further configured to automatically generate, responsive to the indication, at least one additional plurality of 2D images of equally spaced planes which are orthogonal to at least one of the equally spaced planes of the first plurality of 2D images, and wherein the image sequencer is configured to produce at least one additional sequence of 2D images of the at least one additional plurality of 2D images.

16. The ultrasonic diagnostic imaging system of claim 3, wherein the specified plane-to-plane spacing is preprogrammed into the ultrasonic diagnostic imaging system.

17. The ultrasonic diagnostic imaging system of claim 16, wherein the specified plane-to-plane spacing corresponds to a minimum preprogrammed plane-to-plane spacing.

18. The ultrasonic diagnostic imaging system of claim 3, wherein the specified plane-to-plane spacing is set responsive to user input.

19. The ultrasonic diagnostic imaging system of claim 3, wherein the user interface is configured to receive user input indicative of the specified plane-to-plane spacing, the specified number of cut planes, and the entire portion of the volumetric region; and
provide a warning if the specified number of cut planes and plane-to-plane spacing define a volume larger than the entire portion of the volumetric region.

20. The ultrasonic diagnostic imaging system of claim 3, wherein the multiplanar reformatter is configured to receive an indication of one of: (i) the specified plane-to-plane spacing or (ii) the specified number of cut planes, and to automatically determine:
when the indication indicates the specified plane-to-plane spacing, a number of cut planes such that the first plurality of 2D images of the first plurality represents the entire portion of the volumetric image; or
when the indication indicates the specified number of cut planes, a plane-to-plane spacing such that the first plurality of 2D images of the first plurality represents the entire portion of the volumetric region.

21. The ultrasonic diagnostic imaging system of claim 20, wherein the entire portion of the volumetric region is the entire volumetric region.

\* \* \* \* \*